(12) United States Patent
Bortolo et al.

(10) Patent No.: US 6,680,413 B2
(45) Date of Patent: Jan. 20, 2004

(54) PROCESS FOR THE RECOVERY OF PHENOL AND BIPHENOLS

(75) Inventors: Rossella Bortolo, Novara (IT); Lino Carnelli, Carbonate (IT); Daniele Moscotti, Brugherio (IT); Daniele Bianchi, Arese (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/442,089

(22) Filed: May 21, 2003

(65) Prior Publication Data

US 2003/0221948 A1 Dec. 4, 2003

(30) Foreign Application Priority Data

May 31, 2002 (IT) ..................... MI2002A1187

(51) Int. Cl.⁷ .............................................. C07C 37/68
(52) U.S. Cl. ...................................................... 568/759
(58) Field of Search .......................................... 568/759

(56) References Cited

U.S. PATENT DOCUMENTS 6,133,487 A  * 10/2000 Ungarelli

* cited by examiner

*Primary Examiner*—Michael L. Shippen
(74) *Attorney, Agent, or Firm*—Oblon, Spivak, McClelland, Maier & Neustadt, P.C.

(57) ABSTRACT

A process is described for the recovery of phenol and biphenols from their homogeneous mixtures containing benzene, sulfolane and water, which is based on the use of an alkaline solution and benzene for the separation of biphenols from sulfolane, after removing the benzene, $H_2O$ and phenol contained in the reaction effluent.

Figure 1:
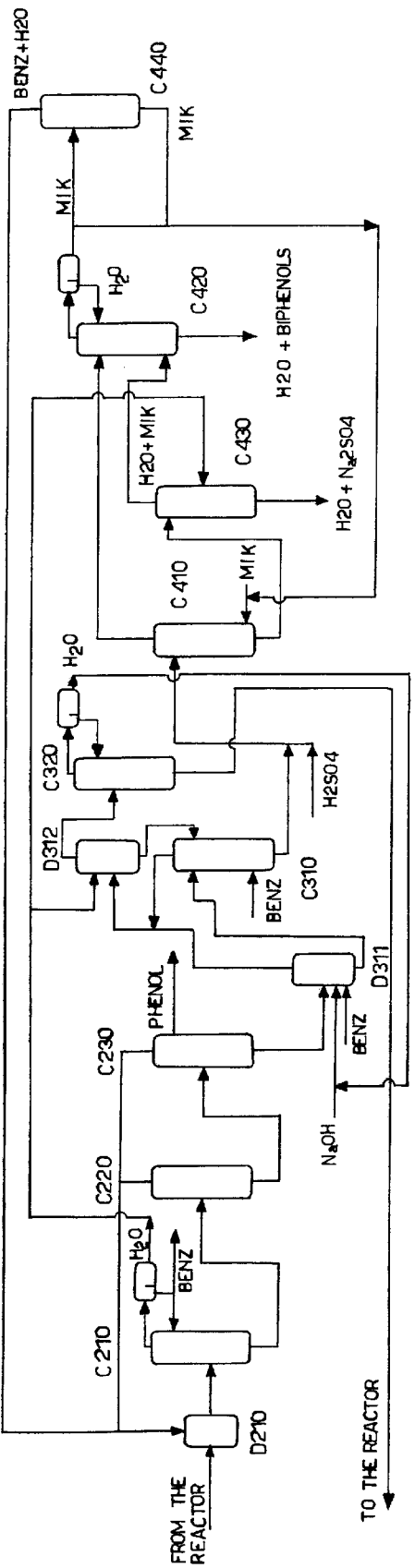

The process allows the recovery of phenol and biphenol by-products dissolved in sulfolane, directly obtaining the purified solvent containing the benzene necessary for the feeding to the reactor for the direct oxidation of benzene, as well as the biphenols dissolved in water and pure phenol.

9 Claims, 1 Drawing Sheet

PROCESS FOR THE RECOVERY OF PHENOL AND BIPHENOLS

The present invention relates to a process for the recovery of phenol and biphenol by-products from solutions containing them.

In particular, the present invention relates to a process for the recovery of phenol and biphenol by-products from their homogeneous mixtures containing benzene, sulfolane and water.

Phenol is a useful product in the preparation of synthetic resins, insecticides and antioxidants.

In industry, phenol is normally prepared by means of benzene alkylation with propylene to give isopropyl benzene, oxidation to the corresponding tert-hydroperoxide and subsequent cleavage to phenol and acetone in the presence of an acid catalyst.

The reaction mixture, after neutralization of the residual acid, is subjected to a series of subsequent distillations for the separation of products and by-products from the non-converted reagents which are recycled to the reaction.

A process has recently been proposed for the production of phenol by means of the direct oxidation of benzene with hydrogen peroxide, in the presence of titanium silicalite, which operates in liquid phase in the presence of sulfolane, as reaction solvent (U.S. Pat. No. 6,133,487).

The process which allows the oxidation of benzene to phenol to be obtained with high yields, is always accompanied by subsequent reactions which lead to the formation poly-hydroxylated products (mainly biphenols), in concentrations varying according to the reaction conditions.

The reaction effluent consequently contains the sulfolane solvent, non-converted benzene, the water formed and that introduced with the diluted hydrogen peroxide, in addition to the phenol, biphenols and tars produced.

In this case, the application of the traditional purification process, which includes the sequential distillation of the various components, is not suitable as, after the separation of the most volatile products (benzene, water and phenol), the distillation of the sulfolane would be required for removing the by-products having a higher boiling point than the solvent.

This solution, in addition to being uneconomical, does not allow the separation of the biphenols—such as catechol, for example—which together with sulfolane form an azeotropic mixture with the highest temperature.

In the present case, it is not even possible to resort to simple extraction with soda in water solution (U.S. Pat. No. 5,338,453), as sulfolane is miscible with water in all proportions.

It has now been found that it is possible to overcome the above-mentioned drawbacks of the known technique by means of the process of the present invention which is based on the use of an alkaline solution and benzene for the separation of biphenols from sulfolane, after the removal of the benzene, $H_2O$ and phenol contained in the reaction effluent.

The process of the present invention allows the recovery of the biphenol by-products dissolved in sulfolane, directly obtaining the purified solvent containing the benzene necessary for the feeding to the reactor for the direct oxidation of benzene, in addition to biphenols dissolved in water and pure phenol.

In accordance with the above, an objective of the present invention is a process for the recovery of phenol and biphenols from their homogeneous mixtures containing benzene, sulfolane and water, which comprises the following steps:

(a) feeding the reaction mixture containing benzene, water, phenol, sulfolane and the reaction by-products (biphenols), to a distillation unit consisting of two or more columns, to obtain one or more products at the head, essentially consisting of the benzene-water azeotropic mixture and phenol, and a product at the bottom, consisting of sulfolane, residual phenol and reaction by-products;

(b) feeding the benzene-water azeotropic mixture to a condensation system consisting of one or more condensers in series in which, after de-mixing, an aqueous phase and a benzene phase are separated. The latter is partially sent back to the distillation unit as reflux, whereas the aqueous phase is totally collected;

(c) feeding the bottom product coming from the distillation unit of step (a), a basic water solution and benzene to one or more mixers and separators (D311) to effect the salification of the biphenols in order to obtain the demixing of the system into an organic phase consisting of benzene and sulfolane and an aqueous phase consisting of water, biphenol salts and a part of sulfolane;

(d) feeding the aqueous phase coming from the mixer/separator (D311) and benzene to a liquid/liquid extraction column (C310) to obtain, at the head, an organic extract saturated with water containing benzene and sulfolane and, at the bottom, a refined product containing phenoL salts in water solution;

(e) feeding the organic phases coming from steps (c) and (d) and water to a mixing/de-mixing system (D312) to obtain an organic stream containing sulfolane, benzene and water and an aqueous stream, saturated with organic products, which is sent to the extraction column C310;

(f) feeding the organic phase coming from step (e) to a distillation column C320 wherein the heterogeneous benzene-water azeotropic mixture with the highest pressure separates at the head, and a product consisting of sulfolane, benzene and residual water separates at the bottom;

(g) feeding the azeotropic mixture obtained in step (f) to a condensation system consisting of one or more condensers wherein an aqueous phase separates and is completely removed and used for preparing the basic aqueous solution to be adopted for the salification of phenols and a benzene phase which is sent back to the column as reflux;

(h) feeding the refined product leaving the extraction column C310 to a mixer and acidifying with an inorganic acid or $CO_2$ to release phenols from their salts;

(i) feeding the aqueous saline solution obtained in step (h) and an extracting agent to an extraction column C410 to obtain an extract containing biphenols, at the head, and a refined product consisting of saline water containing residues of the extracting agent, at the bottom;

(l) feeding the refined product to a distillation column C430 to obtain the residual extracting agent together with water, at the head, and the saline solution, at the bottom, which is sent for disposal or recovery;

(m) feeding the extract leaving the column C410 and the head product of column C430 to a distillation column C420, obtaining the heterogeneous $H_2O$-extraction solvent azeotropic mixture at the head and a solution containing water and biphenols at the bottom;

(n) feeding the head product to a condensation system consisting of one or more condensers wherein an aqueous phase is obtained which is sent as reflux to column C420 of step (m) together with an organic phase containing the extracting agent;

(o) feeding a portion of the organic phase coming from the condenser to a distillation column C440 to obtain a benzene-water mixture at the head, which is recycled to step (a) and the extracting agent at the bottom, which is directly fed to the separation column C410.

According to an embodiment of the present invention, the process comprises:

(a) feeding the reaction mixture containing benzene, water, phenol, sulfolane and reaction by-products to a first distillation column C210 to obtain product at the head, consisting of the benzene-water azeotropic mixture and a product at the bottom, including the residual benzene and water, sulfolane, phenol and by-products;

(b) feeding the benzene-water azeotropic mixture to a condensation system consisting of one or more condensers in series in which, after de-mixing, an aqueous and a benzene phase are separated. The latter is partially sent back to the distillation column as reflux, whereas the aqueous phase is totally collected;

(c) feeding the bottom product leaving the column C210 to a second distillation column C220, to obtain a head product—containing benzene, water and traces of phenol—which is recycled to step (a), and a tail product consisting of phenol, sulfolane and biphenols;

(d) feeding the tail product coming from the distillation column C220 to a third distillation column C230, to obtain pure phenol as a side cut, a distilled product at the head containing possible light products (benzene and water) and an effluent, at the tail, consisting of sulfolane containing residues of phenol and biphenols;

(e) feeding the tail effluent leaving column C230, a basic water solution and benzene to one or more mixers/separators (D311) to obtain the salification of the phenols, feeding benzene in such a quantity as to cause the de-mixing of the system into an organic phase consisting of sulfolane and benzene and an aqueous solution containing the phenol salts and a portion of sulfolane;

(f) feeding the aqueous phase leaving the mixer/separator (D311) and benzene to a liquid/liquid extraction column (C310) to obtain, at the head, an organic extract saturated with water containing benzene and sulfolane and, at the bottom, a refined product containing phenol salts in water solution;

(g) feeding the organic phases coming from steps (e) and (f) and water to a mixing/de-mixing system (D312) to obtain an organic stream containing sulfolane, benzene and water and an aqueous stream, saturated with organic products, which is sent to the extraction column C310;

(h) feeding the organic phase coming from step (g) to a distillation column C320 in which the heterogeneous benzene-water azeotropic mixture with the highest pressure separates at the head, and a product consisting of sulfolane, benzene and residual water separates at the bottom;

(i) feeding the azeotropic mixture obtained in step (h) to a condensation system consisting of one or more condensers wherein an aqueous phase is separated and is completely removed and used for preparing the basic aqueous solution to be adopted for the salification of phenols together with a benzene phase which is sent back to the column as reflux;

(l) feeding the refined product leaving the extraction column C310 to a mixer and acidifying with an organic acid or $CO_2$ to release phenols from their salts;

(m) feeding the aqueous saline solution obtained in step (l) and an extracting agent to an extraction column C410 to obtain an extract containing biphenols, at the head, and a refined product consisting of saline waters, at the bottom;

(n) feeding the refined product to a distillation column C430 to obtain the residual extracting agent together with water, at the head, and the saline solution, at the bottom, which is sent for disposal or recovery;

(o) feeding the extract coming from column C410 and the head product of column C430 to a distillation column C420 obtaining the heterogeneous $H_2O$-extraction solvent azeotropic mixture at the head and a solution containing water and biphenols at the bottom;

(p) feeding the head product to a condensation system consisting of one or more condensers in which an aqueous phase is obtained, which is sent as reflux to column C420 of step (o), together with an organic phase containing the extracting agent;

(q) feeding a portion of the organic phase coming from the condenser to a distillation column C440 to obtain a benzene-water mixture at the head, which is recycled to step (a) and the extracting agent at the bottom, which is directly fed to the separation column C410.

According to an embodiment of the process of the present invention, the reaction effluent, before being fed to the distillation unit, can be subjected to degassing in a flash (D210) in order to remove most of the dissolved inert gases.

The flash operates at a temperature ranging from 20 to 100° C. and at a pressure of between 0.1 and 0.9 bar, preferably at a temperature ranging from 40 to 70° C. and a pressure of between 6.4 and 0.7 bar.

The stream coming from flash is subsequently fed to the distillation system.

The columns C210, C220 and C230 operate under substantially identical temperature conditions at the bottom, i.e. at about 150–200° C., but at different pressures and temperatures at the head.

In particular, the column C210 operates at a pressure ranging from 0.1 to 0.9 bar and a temperature at the head ranging from 20 to 100° C., the column C220 operates at a pressure ranging from 0.5 to 0.1 bar and a temperature at the head ranging from 30 to 100° C., whereas the column C230 operates at a pressure ranging from 0.01 to 0.1 bar and a temperature at the head ranging from 30 to 90° C.

The column C210 has the function of separating benzene and $H_2O$ at the head. The condensed product, after demixing, is separated into aqueous and benzene phases. The latter is partially sent back to the column as reflux, whereas the aqueous phase is totally collected.

The tail effluent of the column contains residual benzene and $H_2O$, to avoid an excessive temperature increase in the boiler.

The exhaustion of the residual benzene and $H_2O$ contained in the tail stream of C210 is effected in a second column (C220), operating at a lower pressure with respect to the preceding one, of which the distillate, also containing phenol, is recycled to C210.

The tail residue of column C220 is sent to a subsequent distillation column (C230) in which pure phenol is obtained as a side cut at the $6^{th}$ step, whereas any possible light products still present are concentrated in the distillate at the headland are recycled to C210.

The tail effluent of C230, consisting of sulfolane containing residual phenol and biphenols, is sent to the biphenol separation section, in which it is first treated with an excess of a basic aqueous solution to salify the phenols present. A solution of NaOH, KOH, $Na_2CO_3$, $K_2CO_3$, $Na_3PO_4$, $K_3PO_4$ is normally used. An NaOH solution is preferably adopted.

Mixing with benzene is subsequently effected, in an amount suitable for causing the de-mixing of the system into an aqueous phase containing the alkaline salts of phenols and a part of sulfolane, and an organic phase consisting of sulfolane and benzene saturated with water.

After separation, the aqueous phase is sent to a liquid-liquid extraction column (C310), where it is treated with benzene to extract the sulfolane contained therein, thus obtaining an extracted product saturated with water, consisting of benzene and sulfolane, and a refined product containing alkaline phenates in water solution.

Part of the extraction solvent comes from the head of C210, the rest consists of the feeding of fresh benzene to reintegrate the amount consumed in the reaction.

The organic phases coming from D311 and C310 are first washed with $H_2O$ in D312 to remove any possible traces of salts contained in the dispersed $H_2O$, and sent to a distillation column (C320) to separate the excess water. The operation is effected by separating the heterogeneous benzene-$H_2O$ azeotropic mixture with the highest pressure at the head.

After de-mixing, the condensate is separated into aqueous and benzene phases. The latter is entirely sent back to the column as reflux, whereas the aqueous phase is totally collected and re-used for the preparation of the alkaline solution to be used for the salification.

The tail effluent of the column (C320) consists of sulfolane, benzene and $H_2O$ in concentrations suitable for recycling the mixture to the reaction.

The refined product, containing sodium phenates in water solution, is fed to a mixer together with an acid, preferably $H_2SO_4$, to release phenols from their salts. The sulfate water solution thus obtained and an extracting agent selected from aromatic hydrocarbons, alcohols, ketones, esters or ethers insoluble or partially soluble in water, particularly cumene, benzene, tert-amyl alcohol, isopropyl ether, 3-pentanone, diisopropyl ketone, butyl acetate, methyl isobutyl ketone, preferably methyl isobutyl ketone (MIK), are fed to an extraction column, producing an extract containing biphenols in the organic solvent and a refined product consisting of sulfate water saturated with said solvent.

The refined product leaving the extraction column is fed to a distillation column for stripping the residual solvent, obtaining sulfate water at the tail, which can be sent for disposal.

A stream of $H_2O$ coming from the head of C210, is also sent to C430, to favour the stripping of the solvent. The column is also equipped with a partial condenser, wherein the condensed product is entirely sent back to the column as reflux.

The recovery of the extraction solvent is effected by sending the extract of C410 and the vapours at the head of the column C430 to the same distillation column (C420), obtaining at the head the heterogeneous azeotropic mixture of $H_2O$-solvent with the highest pressure.

After condensation, the distillate is separated into organic and aqueous phases. The latter is entirely sent back to the column as reflux, whereas the organic phase, consisting of the organic solvent saturated with water, is recycled to the extraction in C410.

Finally, an aqueous solution of biphenols is obtained at the tail.

As the organic solvent distilled in C420 contains a small amount of benzene coming from the previous operations, a part of the solvent (about 5%) must be subjected to distillation in the column C440 to allow the removal of the benzene, thus avoiding its accumulation in the extraction loop.

In this way, a distillate consisting of benzene and $H_2O$ is obtained at the head of the column, which is recycled to C210, whereas the organic solvent devoid of benzene is obtained at the tail.

The process of the present invention can be better understood by referring to the block schemes of FIG. 1, which represents an illustrative but not limitative embodiment thereof.

The following operative example is provided for merely illustrative and non-limiting purposes.

EXAMPLE 1

The scheme of FIG. 1 is followed for the recovery of phenol and biphenols starting from:

a stream coming from a phenol production plant consisting of 36% by weight of benzene, 2% by weight of water, 4% by weight of phenol, 0.4% by weight of biphenols and 57.6% by weight of sulfolane;

an aqueous solution of NaOH and benzene fed to the mixers/separators D311 in such a quantity as to obtain the salification of phenols and cause the de-mixing of the system into an aqueous phase containing the sodium salts of phenols as well as part of the sulfolane, and an organic phase consisting of sulfolane and benzene, respectively;

a solution containing sulfuric acid at 98% by weight, fed to a mixer to release phenols from their salts;

The amounts and data relating to the single streams are shown in Table 1 below.

TABLE 1

| Nr. | Components | Reactor effluent | | Phenol produced | | NaOH water solution | |
|---|---|---|---|---|---|---|---|
| | | Flow rate kg/h | weight % | Flow rate kg/h | weight % | Flow rate kg/h | weight % |
| 1 | Benzene | 230480.031 | 35.9276 | — | — | 87.108 | 0.2449 |
| 2 | $H_2O$ | 15834.952 | 2.4684 | — | — | 32826.020 | 92.3046 |
| 3 | Phenol | 25094.779 | 3.9118 | 25000.000 | 100.0000 | — | — |
| 4 | Catechol | 2150.000 | 0.3351 | — | — | — | — |
| 5 | Hydroquinone | 1080.000 | 0.1684 | — | — | — | — |
| 6 | Tars | 380.000 | 0.0592 | — | — | — | — |

TABLE 1-continued

| Nr. | Components | Flow rate kg/h | weight % | Flow rate kg/h | weight % | Flow rate kg/h | weight % |
|---|---|---|---|---|---|---|---|
| 7 | Sulfolane | 366443.938 | 57.1218 | — | — | — | — |
| 8 | NaOH | — | — | — | — | 2649.585 | 7.4505 |
| 9 | H$_2$SO$_4$ | — | — | — | — | — | — |
| 10 | Na$_2$SO$_4$ | — | — | — | — | — | — |
| 11 | MIK | — | — | — | — | — | — |
| 12 | O$_2$ | 12.602 | 0.0020 | — | — | — | — |
| 13 | N$_2$ | 36.539 | 0.0057 | — | — | — | — |
| | Flow rate (kg/h) | 641512.842 | | 25000.000 | | 35562.713 | |
| | Phase | Liquid | | Liquid | | Liquid | |
| | Temperature (° C.) | 106.11 | | 79.41 | | 60.00 | |
| | Pressure (Atm) | 1.500 | | 0.019 | | 1.000 | |

| | | H$_2$SO$_4$ | | Saline water to be disposed of | | Water solutions of biphenols | |
|---|---|---|---|---|---|---|---|
| Nr. | Components | Flow rate kg/h | weight % | Flow rate kg/h | weight % | Flow rate kg/h | weight % |
| 1 | Benzene | — | — | — | — | — | — |
| 2 | H$_2$O | 66.245 | 2.0000 | 18043.600 | 79.3198 | 9093.807 | 71.0580 |
| 3 | Phenol | — | — | 0.941 | 0.0041 | 93.838 | 0.7332 |
| 4 | Catechol | — | — | — | — | 2150.000 | 16.7999 |
| 5 | Hydroquinone | — | — | — | — | 1080.000 | 8.4390 |
| 6 | Tars | — | — | — | — | 380.000 | 2.9693 |
| 7 | Sulfolane | — | — | — | — | 0.004 | 0.0000 |
| 8 | NaOH | — | — | — | — | — | — |
| 9 | H$_2$SO$_4$ | 3245.985 | 98.0000 | — | — | — | — |
| 10 | Na$_2$SO$_4$ | — | — | 4703.371 | 20.6761 | — | — |
| 11 | MIK | — | — | — | — | 0.080 | 0.0006 |
| 12 | O$_2$ | — | — | — | — | — | — |
| 13 | N$_2$ | — | — | — | — | — | — |
| | Flow rate (kg/h) | 3312.230 | | 22747.910 | | 12797.729 | |
| | Phase | Liquid | | Liquid | | Liquid | |
| | Temperature (° C.) | 50.00 | | 109.60 | | 105.43 | |
| | Pressure (Atm) | 1.000 | | 1.350 | | 1.150 | |

What is claimed is:

1. A process for the recovery of phenol and biphenols from their homogeneous mixtures containing benzene, sulfolane and water, which comprises the following steps:
   (a) feeding the reaction mixture containing benzene, water, phenol, sulfolane and reaction by-products (biphenols), to a distillation unit consisting of two or more columns, to obtain one or more products at the head, essentially consisting of the benzene-water azeotropic mixture and phenol, and a product at the bottom, consisting of sulfolane, phenol and reaction by-products;
   (b) feeding the benzene-water azeotropic mixture to a condensation system consisting of one or more condensers in series in which, after de-mixing, an aqueous and a benzene phase are separated, the latter being partially sent back to the distillation unit as reflux, whereas the aqueous phase is totally collected;
   (c) feeding the bottom product coming from the distillation unit of step (a), a basic water solution and benzene to a mixer/separator to effect the salification of the phenols and obtain the de-mixing of the system into an organic phase consisting of benzene and sulfolane and an aqueous phase consisting of water, phenol salts and a part of sulfolane;
   (d) feeding the aqueous phase coming from the mixer/phase separator (D311) and benzene to a liquid/liquid extraction column (C310) to obtain, at the head, an organic extract saturated with water containing benzene and sulfolane and, at the bottom, a refined product containing the phenol salts in a water solution;
   (e) feeding the organic phases coming from the steps (c) and (d) and water to a mixing/de-mixing system (D312) to obtain, at the head, an organic stream containing sulfolane, benzene and water and an aqueous stream, saturated with organic products, which is sent to the extraction column C310;
   (f) feeding the organic phase coming from step (e) to a distillation column C320 in which the heterogeneous benzene-water azeotropic mixture with the highest pressure separates at the head, and a product consisting of sulfolane, benzene and water separates at the bottom;
   (g) feeding the azeotropic mixture obtained in step (f) to a condensation system consisting of one or more condensers in which an aqueous phase is separated and is completely removed and used for preparing the basic aqueous solution to be adopted for the salification of phenols and also a benzene phase which is sent back to the column as reflux;
   (h) feeding the refined product leaving the extraction column C310 to a mixer and acidifying with an inorganic acid or CO$_2$ to release the phenols from their salts;
   (i) feeding the aqueous saline solution obtained in step (h) and an extracting agent to an extraction column C410 to obtain an extract containing biphenols, at the head, and a refined product consisting of saline water, at the bottom;
   (l) feeding the refined product to a distillation column C430 to obtain the residual extracting agent together with water, at the head, and the saline solution, at the bottom, which is sent for disposal or recovery;
   (m) feeding the extract coming from the column C410 and the head product of column C430 to a distillation column C420 obtaining the heterogeneous azeotropic mixture of $H_2O$-extraction solvent at the head, and a solution containing water and biphenols at the bottom;

(n) feeding the head product to a condensation system consisting of one or more condensers in which an aqueous phase is obtained which is sent as reflux to the column C420 of step (m) and an organic phase containing the extracting agent;

(o) feeding a portion of the organic phase coming from the condenser to a distillation column C440 to obtain a benzene-water mixture at the head, which is recycled to step (a) and the extracting agent at the bottom, which is fed directly to the separation column C410.

2. The process according to claim 1, wherein in step (a) the distillation unit consists of three columns C210, C220 and C230 operating at a temperature at the bottom ranging from 150 to 200° C. and at different pressures and temperatures at the head.

3. The process according to claim 2, wherein the column C210 operates at a pressure ranging from 0.1 to 0.9 bar and a temperature at the head ranging from 20 to 100° C.

4. The process according to claim 2, wherein the column C220 operates at a pressure ranging from 0.05 to 0.1 bar and a temperature at the head ranging from 30 and 100° C.

5. The process according to claim 2, wherein the column C230 operates at a pressure ranging from 0.01 to 0.1 bar and a temperature at the head ranging from 30 to 90° C.

6. The process according to claim 1, wherein in step (c) the basic solution is selected from NaOH, KOH, $Na_2CO_3$, $K_2CO3$, $Na_3PO_4$ and $K_3PO_4$.

7. The process according to claim 1, wherein the acidifying medium in the step (h) is an inorganic acid or $CO_2$.

8. The process according to claim 1, wherein in step (i) the extracting agent is selected from aromatic hydrocarbons, alcohols, ketones, esters or ethers insoluble or partially soluble in water, particularly cumene, benzene, tert-amyl alcohol, isopropyl ether, 3-pentanone, diisopropyl ketone, butyl acetate, methyl isobutyl ketone.

9. The process according to claim 8, wherein the extracting agent is methyl isobutyl ketone.

* * * * *